United States Patent [19]

Lowe

[11] Patent Number: 5,156,431
[45] Date of Patent: Oct. 20, 1992

[54] NEEDLE CAP CLAMP

[76] Inventor: Thomas K. Lowe, 608 East 3rd, Tyler, Tex. 75701

[21] Appl. No.: 671,476

[22] Filed: Mar. 19, 1991

[51] Int. Cl.⁵ .............................................. B25J 1/02
[52] U.S. Cl. ................................... 294/99.2; 606/210
[58] Field of Search ...................... 294/99.2; 81/3, 13, 81/44; 128/917; 606/205, 206, 207, 208, 209, 210

[56] References Cited

U.S. PATENT DOCUMENTS

| | | | |
|---|---|---|---|
| 169,486 | 11/1875 | Sehorn . | |
| 358,928 | 3/1887 | Hart . | |
| 1,368,446 | 2/1921 | Madsen . | |
| 1,874,257 | 8/1932 | Doptis . | |
| 2,563,677 | 8/1951 | Frazier . | |
| 2,608,433 | 8/1952 | Marbeuf . | |
| 2,642,871 | 6/1953 | Thuerig | 606/207 |
| 2,669,992 | 2/1954 | Curutchet | 606/205 |
| 2,685,880 | 8/1954 | Curutchet | 606/210 X |
| 3,101,715 | 8/1963 | Glassman . | |
| 3,316,949 | 5/1967 | Canfield . | |
| 3,320,958 | 5/1967 | Nolan . | |
| 3,367,336 | 2/1968 | Eizenberg | 606/210 |
| 3,777,760 | 12/1973 | Essner | 606/208 X |
| 3,889,995 | 6/1975 | Lin . | |
| 3,906,957 | 9/1975 | Weston | 294/99.2 X |
| 3,977,410 | 8/1976 | Huston et al. . | |
| 4,044,771 | 8/1977 | Wannag | 294/99.2 X |
| 4,079,765 | 3/1978 | Hatayan . | |
| 4,226,459 | 10/1980 | Natalicio . | |
| 4,318,313 | 4/1982 | Tartaglia . | |
| 4,461,297 | 7/1984 | Sutter | 606/210 |
| 4,605,256 | 8/1986 | Stokoe . | |
| 4,666,199 | 5/1987 | Cheh . | |
| 4,717,386 | 1/1988 | Simmons . | |
| 4,767,412 | 8/1988 | Hymanson . | |
| 4,842,586 | 6/1989 | Hogan . | |
| 4,917,243 | 4/1990 | Abrams et al. . | |
| 4,919,656 | 4/1990 | Bracker et al. . | |
| 4,938,514 | 7/1990 | D'Addezio | 294/99.2 X |
| 5,002,561 | 3/1991 | Fisher | 128/917 X |

OTHER PUBLICATIONS

Pro-Tec' TM Safety Fingers Advertisement.
Two Photographs of On-Guard Recapper TM, Patent Pending.

Primary Examiner—Johnny D. Cherry
Assistant Examiner—Joseph D. Pape
Attorney, Agent, or Firm—Hubbard, Thurman, Tucker & Harris

[57] ABSTRACT

A needle cap clamp (10) is a resilient, flexible frame with a right arm (12) and a left arm (14) connected at a base (16). The distal end of each arm is characterized by a curved jaw (20, 22). These jaws are configured to grasp the cap (4) surrounding the needle of a syringe (2). The arms (12, 14) are closed towards each other during grasping. To maintain a closed position, mutually engaging engagement members (28, 30) extend inward from both arms (12, 14). To disengage the jaws (20, 22) from the cap (4), pressure is applied to pressure tab (32) in a direction normal to the primary plane defined by the frame. To ensure alignment of the engagement members (28, 30), a guide peg (40) also extends inward from arm 12 and penetrates a guide peg hole (42) in opposing arm (14). A fixed diameter grasping head (18) penetrates the base (16).

19 Claims, 2 Drawing Sheets

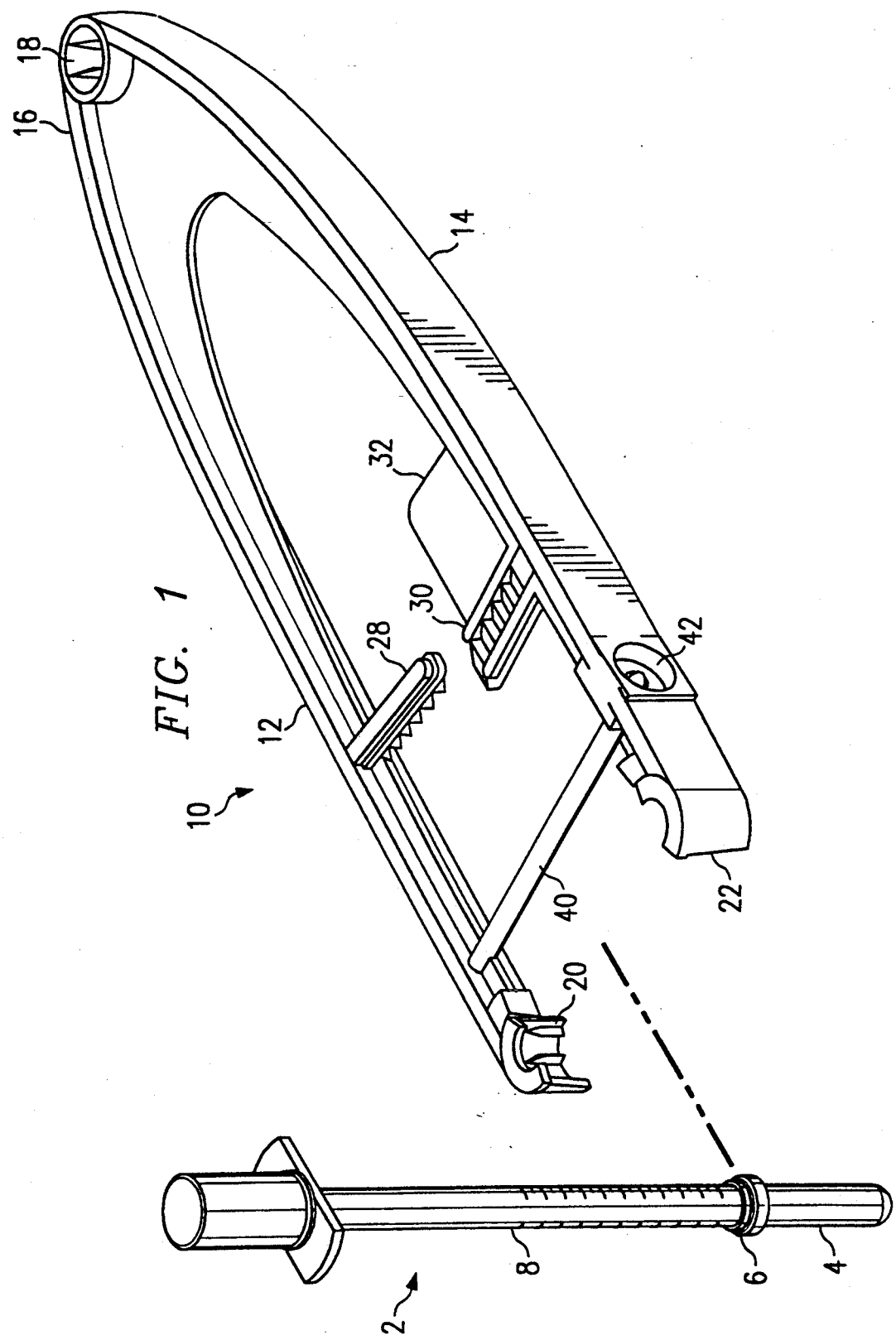

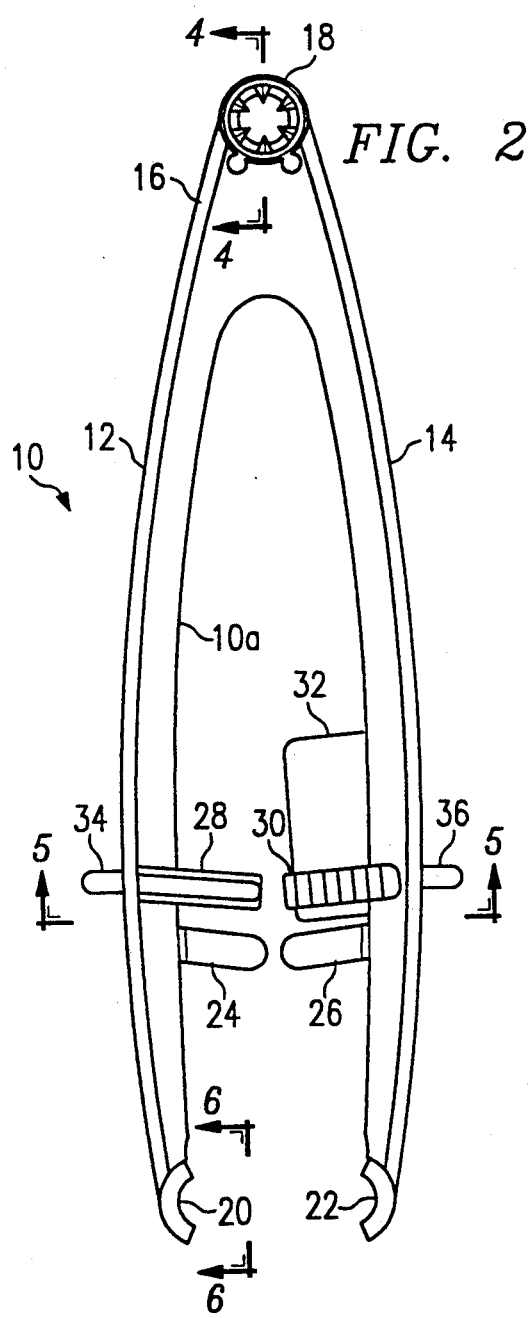
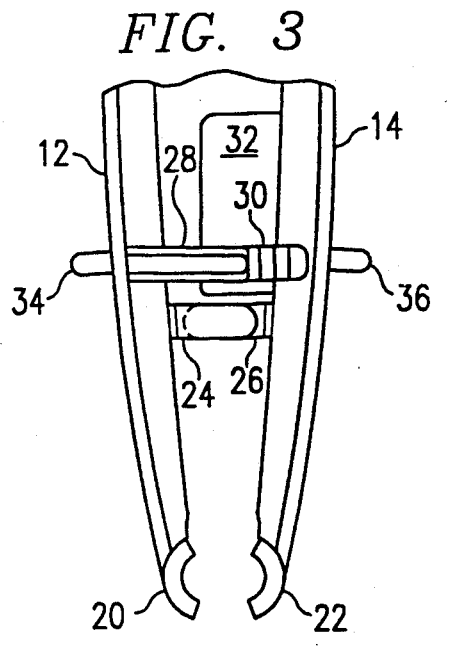
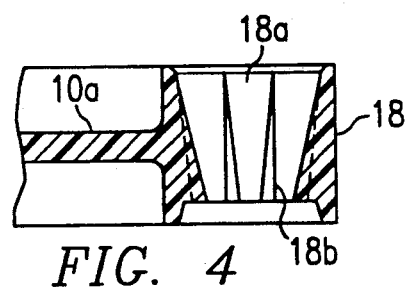
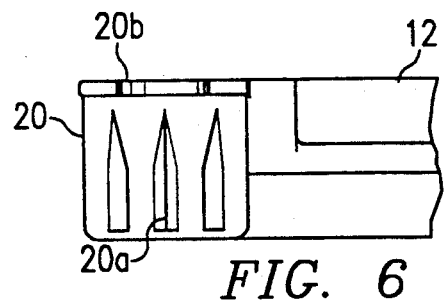
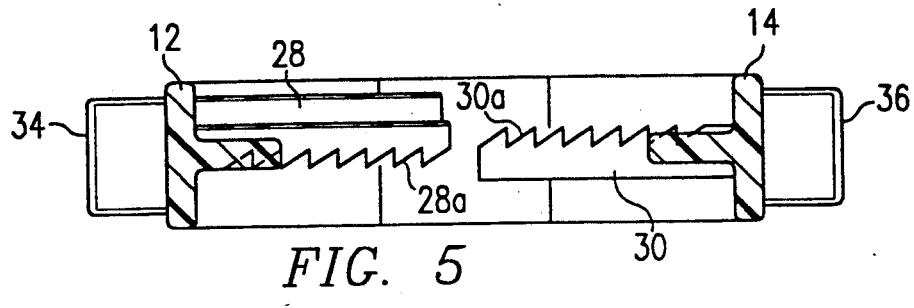

NEEDLE CAP CLAMP

TECHNICAL FIELD OF THE INVENTION

The present invention relates to a grasping device specifically designed to grasp the cap or sheath covering a needle on a syringe.

BACKGROUND OF THE INVENTION

Hypodermic syringes typically have a hollow needle at one end of a cylindrical fluid container and a moveable plunger at the opposite end of the container. The plunger is used to discharge fluid from the cylinder through the needle, or to draw fluid through the needle into the cylinder. The syringe needle should allow for relatively painless entry into the skin. Therefore, the needle may have a relatively small cross section and an extremely sharp tip.

Due to the sharpness of the needle tip, use of the syringe requires great care. Even the most casual contact of the needle with the skin of the health care provider handling the syringe is likely to penetrate the skin, a circumstance commonly known as a "needle stick." Although a needle stick is a minor injury, it carries the threat of transmitting such dangerous diseases as hepatitis and AIDS from the patient receiving an injection to the health care provider. Furthermore, potentially lethal drugs or toxins can also be accidently transmitted by a needle stick.

Due to the sharpness and delicate structure of the syringe needle, a removable protective sheath or cap, usually made of plastic, is installed over the needle. The protective sheath is an elongated sleeve, slightly longer than the needle. The sheath is relatively narrow and protects the needle while permitting safe handling of the syringe when the syringe is not in use. Before using the syringe, the protective sheath must be removed from the needle, a procedure known as uncapping. During uncapping, the sheath is normally gripped between the fingers of one hand, while the other hand holds the cylinder or main body portion of the syringe. After the syringe has been used, the protective sheath is often replaced over the needle, a procedure known as recapping. Unfortunately any distraction, any shake of the hand, and any misalignment of the needle and sheath during recapping is likely to result in a needle stick to the hand which holds the sheath.

Several devices have been constructed to protect against accidental needle sticks. For example, U.S. Pat. No. 4,717,386 to Simmons discloses a safety device for a needle. The device comprises a paddle-shaped member that includes a hand shield section. A handle extends from the hand shield section. A sheath or cap retainer is formed or otherwise provided at a central portion of the hand shield section. The cap retainer includes a recess having a countersink, a reduced midportion and a reduced end portion, thus providing stepped edges.

U.S. Pat. No. 4,767,412 to Hymanson discloses a finger guard for use with a storage tube for a hypodermic needle to prevent accidental injury. The finger guard comprises a tubular finger gripping portion having a bore therein in which the storage tube is received. Radially inwardly extending deformable flaps grip the storage tube, whereby differing sizes of storage tube may be accommodated. An annular guard portion extends radially outwardly of the finger grip portion at the forward end of the guard to prevent the needle from contact with the fingers when attempting to insert the needle into the storage tube.

U.S. Pat. No. 4,919,656 to Bracker et al. discloses a safety device for a hypodermic syringe. The device is a rigid plastic disk which bites into and displaces material on the shell portion of a needle cover cap to protect a user from accidental stick injuries while recapping the needle. The disk has a central aperture which is formed of a plurality of radially projecting teeth.

Needle sticks to the hands are a prevalent work site accident in hospitals, physician's offices and medical laboratories. The risk of disease or drug transmission from needle sticks makes it desirable to have a device for uncapping and recapping the protective sheath of a syringe while minimizing the risk of needle sticks to the hands. Such a device should be able to releasably clamp the protective sheath and to exert removal or reattachment pressure thereon. Such a device should also be resilient, simple to handle, and simple to manufacture.

SUMMARY OF THE INVENTION

The present invention relates to a needle cap clamp that is designed to releasably grip the sheath or cap covering the needle of a syringe. The needle cap clamp is comprised of a one-piece, resilient, frame. The frame is generally U-shaped with a left arm and an opposing right arm. The frame defines a primary plane. Both arms are attached at a base. The frame is dimensioned to be easily gripped in either hand. Finger stop tabs extend outward from each arm to ensure a secure grip and to keep the operating hand away from the needle.

Each arm may be flexed toward the opposing arm by the exertion of closure pressure on each arm. This movement occurs in the primary plane. Engagement means extend inward from each arm. Thus, when the arms are flexed toward each other, each arm's engagement means engages the other arm's engagement means, locking the flexed arms in a closed position. The engagement means, typically complementary teeth, allow for a number of closure positions. To ensure that the engagement means are aligned, guide tabs also extend inward from each arm. These guide tabs inhibit movement of the arms normal to the primary plane. On the end of each arm is a curved jaw. Both the right and left jaw create a grasping head, each with its concave side inward. Each jaw is curved with a plurality of inwardly directed ridges extending therefrom. The bottom edge surface of each jaw is flanged to create a pressure exerting surface.

In operation the jaws are placed around the object to be grasped, typically a cap over a needle on a syringe. The arms are then flexed toward each other, bringing the jaws into grasping engagement with the cap. The engagement means engage each other, locking the arms in position and maintaining the jaw's grasp of the cap. The needle may now be uncapped and recapped. After recapping, the jaws are disengaged from the cap by applying pressure to a pressure tab which extends outward from one arm. This pressure is applied normal to the primary plane in the direction necessary to separate the engagement means. In addition to the jaws, a fixed diameter hole penetrates the base. The walls defining the hole are ridged. Thus, a capped needle may be wedged into this hole, and the cap removed.

BRIEF DESCRIPTION OF THE DRAWINGS

For a more complete understanding of the present invention, and for further details and advantages thereof, reference is now made to the following Detailed Description taken in conjunction with the accompanying drawings, in which:

FIG. 1 is a perspective view of the needle cap clamp in its open position;

FIG. 2 is a top view of an alternate embodiment of the needle cap clamp;

FIG. 3 is a partial top view of the needle cap clamp in a closed position;

FIG. 4, is a longitudinal sectional view of a ratcheted hole in the base of the needle cap clamp;

FIG. 5 is a sectional view through the clamp engagement means; and

FIG. 6 is a partial side view of the inside of one opposing jaw.

DETAILED DESCRIPTION

The present invention is a needle cap clamp that overcomes many of the disadvantages found in the prior art. Referring to FIG. 1, a needle cap clamp 10 embodying the present invention is shown adjacent syringe 2. The clamp is typically a single molded unit with opposing arms 12, 14 connected at base 16. The clamp 10 is shown in an open position, prepared to grasp cap 4 from syringe 2. Cap 4 is positioned over a needle (not shown) which is in fluid communication with cylinder 8. The cap is typically made of a material such as polycarbonate and may be any suitable color.

FIG. 1 further illustrates engagement means 28, 30 and extending inward from arms 12 and 14, respectively. A guide peg 40 may extend inward from arm 12 and penetrate guide peg hole 40 in arm 14. The guide peg 40 is shown more distal to base 16 than engagement means 28, 30; however, their positions may be reversed. At the distal ends of arms 12 and 14 are opposing jaws 20, 22 respectively. These jaws 20, 22 create a grasping means. Penetrating the base 16 is another grasping means, ratcheted hole 18.

In operation the clamp 10 is grasped in one's hand. Next, the clamp is positioned so that jaws 20, 22 surround cap 4 of syringe 2. The clamp 10 is then compressed until arms 12 and 14 engage cap 4. Specifically, flanges on jaws 20 and 22 complement groove 6. Engagement means 28 and 30 engage each other locking the clamp in a closed position. Guide peg 40 ensures alignment of jaws 20, 22 and engagement means 28, 30. The cap 4 may now be removed and subsequently replaced without risk of an accidental needle stick. After recapping, the clamp 10 may be disengaged from cap 4 by application of pressure to pressure tab 32. This pressure is applied normal to the primary plane defined by the clamp 10. Furthermore, the pressure must be applied in the direction necessary to separate engagement means 28, 30. During disengagement, the guide peg 40 should be flexible enough to allow for the movement of arms 12 and 14 normal to the primary plane. FIG. 2 illustrates substantially the same embodiment as shown in FIG. 1 except guide tabs 24, 26 replace guide peg 40 and guide peg hole 42. Guide tabs 24, 26 also ensure the alignment of engagement means 28, 30 and opposing jaws 20, 22. FIG. 2 also illustrates stop tabs 34, 36 extending outward from arms 12 and 14 respectively. These tabs 34, 36 allow the clamp to be grasped securely. Ridge 10*l* adds rigidity to clamp 10.

FIG. 3 illustrates clamp 10 in a closed position. Jaws 20 and 22 form a substantially circular grasping head. The diameter of this grasping head may be varied to accommodate needle caps of different sizes. Furthermore, the diameter of the grasping head is maintained by engagement means 28, 30. Thus, engagement means 28, 30 must allow for a plurality of closure positions. Guide tabs 24 and 26 overlap each other when the clamp 10 is in a closed position.

FIG. 4 illustrates the ratcheted grasping head 18 located in base 16 of clamp 10. A hole 18a penetrates the width of base 16. A plurality of ridges 18b are spaced around the gently sloped interior wall defining hole 18. These ridges 18b increase in width from top to bottom. In operation, the cap 4 on syringe 2 (not shown) is inserted into hole 18a until it wedges into ridges 18b. The clamp 10 is then rotated, facilitating the removal of cap 4. Due to the configuration of ridges 18b, a range of cap sizes may be removed with grasping head 18.

FIG. 5 provides a more detailed sectional view across engagement means 28 and 30. Engagement means 28 extends inward from arm 12. Engagement means 30 extends inward from arm 14. Teeth 28a complement teeth 30a during engagement, thus locking the clamp arms 12 and 14 in position. The number of closure positions allowed is determined by the number of teeth on each engagement means. Stop tabs 34 and 36 are also shown.

FIG. 6 illustrates the concave face of jaw 20 on arm 12. A plurality of ridges 20a extend outward from the concave face. A flattened flange 20b is located on one edge of jaw 20. This flange 20b is typically adapted to fit into the groove 6 between cap 4 and syringe 2, as best seen in FIG. 1. Therefore, the flange 20b is usually a thin crescent-shaped plate that matches the curve of jaw 20. The flange 20b also is typically as wide as ridges 20a. A corresponding set of ridges 22a and flange 22b exist on jaw 22.

Although preferred embodiments of the invention have been described in the foregoing Detailed Description and illustrated in the accompanying drawings, it will be understood that the invention is not limited to the embodiments disclosed, but is capable of numerous rearrangements, modifications and substitutions of parts and elements without departing from the spirit of the invention. Accordingly, the present invention is intended to encompass such rearrangements, modifications and substitutions of parts and elements as fall within the spirit and scope of the invention.

I claim:

1. An apparatus for removing or replacing a cap onto a needle of a syringe comprising:
   (a) a clamp with a right arm and a left arm;
   (b) means to grasp said cap attached to said right arm and left arm, said means comprising:
      (i) a curved structure with a concave base surface and a top surface, said structure attached to the distal end of said arm such that the concave surface faces the opposing arm;
      (ii) a flange extending from the top surface; and
      (iii) a plurality of tapered ridges extending from the concave surface;
   (c) means to engage said clamp in at least one closed position; and
   (d) means to disengage said clamp from at least one closed position.

2. The apparatus of claim 1 wherein said clamp is comprised of a resilient material.

3. The apparatus of claim 1 wherein said clamp is U-shaped.

4. The apparatus of claim 1 wherein said means to grasp is comprised of opposing jaw members respectively attached to said right and left arms.

5. The apparatus of claim 1 wherein said means to engage said clamp is comprised of complementary engaging teeth extending inward both the right and left arm.

6. The apparatus of claim 1 wherein said means to disengage is comprised of a pressure tab attached to either arm of said clamp adjacent said means to engage.

7. An apparatus for removing or replacing a cap onto a needle of a syringe comprising:
  (a) a U-shaped frame with a right arm and a left arm extending from a base;
  (b) a jaw attached to the distal end of each of said arms, said jaw comprising:
    (i) a curved structure with a concave base surface and a top surface, said structure attached at one end of the distal end of said arm such that the concave surface faces the opposing arm;
    (ii) a flange extending from the top surface; and
    (iii) a plurality of tapered ridges extending from the concave surface;
  (c) complementary engagement means extending inward from a medial portion of each of said arms;
  (d) means to disengage said engagement means attached to one of said arms;
  (e) a fixed diameter grasping means penetrating said base.

8. The apparatus of claim 7 further comprises:
  (f) stop tabs extending outward from a medial portion of each of said arms.

9. The apparatus of claim 7 wherein said U-shaped frame is resilient.

10. The apparatus of claim 7 wherein said complementary engagement means comprises a toothed finger extending inward from each said arm, said toothed fingers dimensioned to engage and lock with each other.

11. The apparatus of claim 7 wherein said means to disengage said engagement means comprises a pressure tab attached to an arm adjacent an engagement means.

12. The apparatus of claim 7 wherein said fixed diameter grasping means comprises:
  (a) a hole penetrating the base of the frame;
  (b) a plurality of tapered ridges extending outward into the hole from the frame defining the hole.

13. The apparatus of claim 8 wherein each of said stop tabs comprises a rigid projection extending outward from the medial portion of each arm.

14. The apparatus of claim 7 further comprises:
  (f) guide means attached to said right arm and left arm.

15. The apparatus of claim 14 wherein said guide means comprises:
  (a) a guide peg extending inward from an arm; and
  (b) a guide peg hole positioned on the opposing arm to accept said guide peg.

16. The apparatus of claim 14 wherein said guide means comprises:
  (a) a first guide tab extending inward from an arm;
  (b) a second guide tab extending inward from the opposing arm in sliding relationship to said first guide tab.

17. The apparatus of claim 8 further comprises:
  (g) guide means attached to said right arm and left arm.

18. An apparatus for removing or replacing a cap onto a needle of a syringe comprising:
  (a) a U-shaped frame with a right arm and a left arm extending from a base;
  (b) a jaw attached to the distal end of each of said arms;
  (c) complimentary engagement means extending inward from a medial portion of each of said arms;
  (d) means to disengage said engagement means;
  (e) a fixed diameter grasping means penetrating said base, said fixed diameter grasping means comprising:
    (i) a hole penetrating the base of the frame;
    (ii) a plurality of tapered ridges extending outward into the hole from the wall defining the hole.

19. An apparatus for removing or replacing a cap onto a needle of a syringe comprising:
  (a) a U-shaped frame with a right arm and a left arm extending from a base;
  (b) a jaw attached to the distal end of each of said arms, said jaws comprising:
    (i) a curved structure with a concave surface and a top surface, said structure attached to one end of the distal end of said arm such that the concave surface faces the opposing arm;
    (ii) a flange extending from the top surface; and
    (iii) a plurality of tapered ridges extending from the concave surface;
  (c) complimentary engagement means extending inward from a medial portion of each of said arms;
  (d) means to engage said engagement means;
  (e) a fixed diameter grasping means penetrating said base, said fixed diameter grasping means comprising:
    (i) a hole penetrating the base of the frame;
    (ii) a plurality of tapered ridges extending outward into the hole from the wall defining the hole.

* * * * *

UNITED STATES PATENT AND TRADEMARK OFFICE
CERTIFICATE OF CORRECTION

PATENT NO. : 5,156,431
DATED     : October 20, 1992
INVENTOR(S) : Thomas K. Lowe It is certified that error appears in the above-indentified patent and that said Letters Patent is hereby corrected as shown below:

Column 3, line 68, delete [10/] and insert --10a--.

Column 5, line 8, insert --from-- after "inward".

Column 5, line 19, delete [base].

Column 6, line 37, "jaws" should be --jaw--.

Signed and Sealed this

Twenty-eighth Day of September, 1993

Attest:

BRUCE LEHMAN

Attesting Officer    Commissioner of Patents and Trademarks